United States Patent
Kolter et al.

(10) Patent No.: US 8,962,064 B2
(45) Date of Patent: Feb. 24, 2015

(54) PRODUCTION OF PULVERULENT COATING COMPOSITIONS FOR STABLE PROTECTIVE COATINGS FOR PHARMACEUTICAL DOSAGE FORMS

(75) Inventors: Karl Kolter, Limburgerhof (DE); Maximilian Angel, Schifferstadt (DE); Bernhard Linner, Bobenheim-Roxheim (DE)

(73) Assignee: BASF SE, Ludwigshafen (DE)

( * ) Notice: Subject to any disclaimer, the term of this patent is extended or adjusted under 35 U.S.C. 154(b) by 127 days.

(21) Appl. No.: 13/406,641

(22) Filed: Feb. 28, 2012

(65) Prior Publication Data

US 2012/0219695 A1    Aug. 30, 2012

Related U.S. Application Data

(60) Provisional application No. 61/447,123, filed on Feb. 28, 2011.

(51) Int. Cl.
| | | |
|---|---|---|
| *A61K 9/28* | (2006.01) | |
| *A61K 47/32* | (2006.01) | |
| *C09D 5/03* | (2006.01) | |
| *C09D 133/26* | (2006.01) | |

(52) U.S. Cl.
CPC . *A61K 47/32* (2013.01); *C09D 5/03* (2013.01); *C09D 133/26* (2013.01); *A61K 9/2846* (2013.01); *C08L 2201/54* (2013.01)
USPC .... 427/2.14; 525/186; 428/423.7; 424/130.1; 427/2.1; 427/2.24; 427/2.25; 427/420

(58) Field of Classification Search
USPC ............. 428/423.7; 424/130.1; 525/186; 260/885
See application file for complete search history.

(56) References Cited

U.S. PATENT DOCUMENTS

| | | | |
|---|---|---|---|
| 3,660,537 A * | 5/1972 | Fryd et al. ............. | 525/293 |
| 4,433,076 A | 2/1984 | Bauer et al. | |
| 4,913,970 A * | 4/1990 | Hayward et al. .......... | 428/423.7 |
| 5,304,607 A * | 4/1994 | Marrion .............. | 525/186 |
| 6,281,282 B1 | 8/2001 | Breitenbach et al. | |
| 6,624,210 B1 | 9/2003 | Petereit et al. | |
| 6,696,085 B2 | 2/2004 | Rault et al. | |
| 2003/0064036 A1 | 4/2003 | Petereit et al. | |
| 2004/0249035 A1 | 12/2004 | Petereit et al. | |
| 2005/0079216 A1 | 4/2005 | Petereit et al. | |
| 2005/0271778 A1 | 12/2005 | Petereit et al. | |
| 2005/0281871 A1 | 12/2005 | Petereit et al. | |
| 2009/0136480 A1 * | 5/2009 | Glenn et al. ............. | 424/130.1 |
| 2011/0033532 A1 | 2/2011 | Angel et al. | |

FOREIGN PATENT DOCUMENTS

| | | |
|---|---|---|
| CA | 1009144 | 4/1977 |
| DE | 1090381 | 10/1960 |
| DE | 1219175 | 6/1966 |
| DE | 2135073 | 2/1973 |
| DE | 2512238 | 5/1976 |
| DE | 3049179 | 7/1982 |
| EP | 0088951 | 9/1983 |
| EP | 0262326 | 4/1988 |
| EP | 0901787 | 3/1999 |
| GB | 1097054 | 12/1967 |
| WO | WO-97/42255 | 11/1997 |
| WO | WO-00/05307 | 2/2000 |
| WO | WO-02/067906 | 9/2002 |
| WO | WO-2004/019918 | 3/2004 |
| WO | WO-2009/016258 | 2/2009 |
| WO | WO-2011/012335 | 2/2011 |
| WO | WO-2011/051155 | 5/2011 |
| WO | WO-2012/031934 | 3/2012 |
| WO | WO-2012/041788 | 4/2012 |
| WO | WO-2012/116941 | 9/2012 |

OTHER PUBLICATIONS

"Machine Translation of DE1090381", 2 pages.
PCT International Search Report in PCT/EP2012/053231, dated Apr. 26, 2012, 4 pgs.

* cited by examiner

*Primary Examiner* — Dah-Wei D Yuan
*Assistant Examiner* — Andrew Bowman
(74) *Attorney, Agent, or Firm* — Servilla Whitney LLC

(57) ABSTRACT

Described is a process for producing pulverulent, antioxidant-comprising coating compositions, comprising providing an aqueous polymer dispersions comprising one or more antioxidants and a polymer obtained by radical polymerization of
  a) N,N-diethylaminoethyl methacrylate, and
  b) at least one radically polymerizable compound selected from esters of $\alpha,\beta$-ethylenically unsaturated mono- and dicarboxylic acids with $C_1$-$C_8$-alkanols,
wherein the antioxidants are incorporated into the aqueous polymer dispersion in the form of a solution or of a dispersion, and spray processing the aqueous polymer dispersion to provide a powder form.

16 Claims, No Drawings

PRODUCTION OF PULVERULENT COATING COMPOSITIONS FOR STABLE PROTECTIVE COATINGS FOR PHARMACEUTICAL DOSAGE FORMS

CROSS-REFERENCE TO RELATED APPLICATIONS

This application claims priority under 35 U.S.C. §119(e) to U.S. Provisional Application No. 61/447,123, filed Feb. 28, 2011, the disclosure of which is incorporated herein by reference in its entirety.

FIELD OF THE INVENTION

Embodiments of the present invention relate to the production of coating compositions for stable protective coatings for pharmaceutical dosage forms.

BACKGROUND

For the provision of binders for drug coatings with a low residual monomer content, DE-B 2512238 teaches the use of a powder obtained by spray drying a polymer dispersion for producing coating solutions for these drug forms. With regard to the dispersions used for the spray drying, reference is made to DE 1090381, DE 1219175 and DE 2135073.

DE 3049179 A1 is an application of addition to DE 2512238 and relates to the use of a powder obtained by spray drying according to the teaching of the last-mentioned document in the form of an aqueous suspension, which additionally comprises a plasticizing agent, for producing coatings by thermogelation.

WO 00/05307 deals with the provision of coating and binding compositions for drug forms which comprise (meth) acrylate copolymers which have monomer radicals with tertiary amino groups, the intention being for simple dry or aqueous further processing to be possible. In addition, this document teaches a process in which (a) a copolymer of $C_1$-$C_4$-esters of (meth)acrylic acid and (meth)acrylate monomers which have tertiary ammonium groups, (b) a plasticizer and (c) an emulsifier with an HLB value of at least 14 are combined with one another and the coating or binding composition is produced therefrom by melting, pouring, spreading or spraying, where the copolymer (a) is incorporated in powder form with an average particle size from 1 to 40 μm. The processability achieved here is attributed to the provision of the copolymer (a) in powder form with an extremely small particle size.

WO 02/067906 relates to coating and binding compositions having improved water-vapor permeability compared with those described in WO 00/05307. Here, the coating and binding compositions are produced using a mixture which comprises (a) a copolymer of $C_1$-$C_4$-esters of (meth)acrylic acid and further (meth)acrylate monomers with functional tertiary ammonium groups in powder form having an average particle size from 1 to 40 μm, (b) an emulsifier with an HLB value of at least 14 and (c) a $C_{12}$-$C_{18}$-monocarboxylic acid or a $C_{12}$-$C_{18}$-hydroxyl compound.

WO 2004/019918 describes coating and binding compositions which correspond to those described in WO 00/05307 and WO 02/067906 as regards their composition.

According to U.S. Pat. No. 6,696,085 B2, a methacrylic acid copolymer type C is reportedly used as disintegrant. The methacrylic acid copolymer type C is an enteric polymer which is not soluble in the acidic pH range, but is water-soluble in the pH range of 7, as is present in the oral cavity. Besides a low fracture strength (<20N), the tablets have a high friability (>7%) and include a high proportion, in the region of 15% by weight, of coarsely particulate disintegrant. Consequently, they have low mechanical strength and, on account of the high proportion of coarsely particulate disintegrant, have an unpleasant sandy feel in the mouth.

EP88951 A2 describes a process for coating drugs using a water-dispersed coating composition based on emulsion polymers, where the coating compositions may be partially present in salt form. The coating compositions can also be obtained from redispersed powders, with the processes of spray drying and of freeze drying being specified as methods that are suitable in principle. However, in this connection, it is also stated that the freeze drying may also be able to be used at the lower limit of the range of suitable glass transition temperatures. Either powders obtained by freeze drying or a spray-dried product of 30% methacrylic acid and 70% methyl methacrylate, which has a high glass transition temperature on account of its composition, are specifically described.

WO 97/42255 describes the spray drying of polymer powders that can be redispersed in aqueous solution and comprise free acid- or base-carrying copolymers by spray drying, where, before the spray drying, the pH values of the dispersions have to be adjusted with the help of a buffer system.

EP 262326 A2 describes a process for producing a redispersible plastics polymer in which an aqueous dispersion of a copolymer of (meth)acrylic acid and (meth)acrylic acid esters with a minimum film-forming temperature below 60° C. and a dynamic glass transition temperature below 150° C. is spray dried such that the entry temperature of the drying gas is above the minimum film-forming temperature and below the glass transition temperature.

EP 901 787 A1 describes stabilized pharmaceutical preparations comprising active ingredients that are sensitive to decomposition by light or free radicals and which are coated with a coating composition which, besides metal oxides, basic substances and plasticizers, comprises free radical scavengers for stabilizing the active ingredients. Base materials that are mentioned for the coating compositions are all materials that are possible in principle, such as sugars, cellulose derivates, polyvinylpyrrolidones or (meth)acrylate polymers. It is also mentioned that the coating compositions can comprise aminoalkyl methacrylate polymers as slow-release polymers.

WO 2009/016258 discloses the production of the aqueous polymer dispersions of cationic polymers based on N,N-diethylaminoethyl methacrylate as are used according to the invention and the use thereof for the coating of drugs. Pulverulent coating compositions are only mentioned in quite general terms. On account of their low glass transition temperature, under certain circumstances, the polymers exhibit an undesired tendency towards agglomeration and therefore make high demands from a processing point of view. Special methods for stabilization for example against discoloration upon storage or for achieving release stability even upon prolonged storage or under stress are not mentioned.

There is a need for free-flowing pulverulent film coating compositions with good redispersibility in water which are suitable for pharmaceutical dosage forms which, even upon prolonged or thermally demanding storage, have no change in the release behavior of the film coatings and no discoloration. One requirement for such redispersed coating compositions is, inter alia, the generation of stable small-particle dispersions with narrow particle size distributions and the avoidance of coagulation. Furthermore, there is a need for polymer dispersions or polymer powders that can incorporate stabilizing substances such as antioxidants without adversely affecting the stability of the polymer dispersion or of the polymer powder and applications-related properties thereof. Also, a further problem is not only incorporating antioxidants which are in most cases sparingly soluble in water into the aqueous dispersion in a homogeneous manner, but also bringing them into contact to an adequate extent with the dispersed polymer particles to allow the water-insoluble antioxidants to migrate into the polymer particles since they are supposed to develop their effect therein. Consequently, there is a need for a process which transports a sparingly water-soluble substance into another phase via such a water phase. This problem is exacerbated by the fact that no plasticizer can be used which could act as entrainer since plasticizers make the conversion of such a preparation into a redispersible powder impossible on account of the onset of film formation.

SUMMARY

One aspect of the present invention pertains to a process for producing pulverulent, antioxidant-comprising coating compositions comprising providing an aqueous polymer dispersion comprising one or more antioxidants and, as component A, a polymer obtained by radical polymerization of
  a) N,N-diethylaminoethyl methacrylate, and
  b) at least one radically polymerizable compound selected from esters of α,β-ethylenically unsaturated mono- and dicarboxylic acids with $C_1$-$C_8$-alkanols,
wherein the antioxidants are incorporated into the aqueous polymer dispersion in the form of a solution or of a dispersion. The aqueous polymer dispersion is then spray processed to provide a powder form.

According to one or more or more embodiments of this aspect, one or more antioxidants are sparingly water-soluble.

In one or more embodiments, the antioxidants are incorporated in the form of a solution in an organic solvent or as a micellar aqueous solution comprising a solubilizer. In some embodiments, the micellar solution of the antioxidants comprises surfactants or amphiphilic copolymers as solubilizers.

One or more embodiments provide that the antioxidants are incorporated in the form of a solid solution of the antioxidants in surfactants or polymers. In some embodiments, the solid solution of the antioxidants in surfactants or polymers is obtained by melt extrusion.

In some embodiments, the antioxidants are incorporated into the aqueous polymer dispersion in the form of a dispersion comprising emulsifiers with a hydrophilic-lipophilic balance value greater than 10.

According to one or more embodiments, the antioxidants are incorporated in amounts of from 0.1 to 10.0% by weight, based on component A.

In further embodiments of this aspect, the aqueous polymer dispersion is converted to powder by spraying processes in the presence of a drying gas. In one or more embodiments, the entry temperature of the drying gas into the spraying apparatus is at least 20° C. above the glass transition temperature and is at least 20° C. above the minimum film-forming temperature of the polymer of the polymer and the exit temperature of the drying gas from the spraying apparatus is maintained at 40 to 85° C.

In one or more embodiments, the entry temperature of the drying gas into the spraying apparatus is at least 40° C. above the glass transition temperature and is at least 40° C. above the minimum film-forming temperature of the polymer. According to one or more embodiments, the entry temperature of the drying gas into the spraying apparatus is at least 20° C. above the dynamic glass transition temperature. In some embodiments, the entry temperature of the drying gas into the spraying apparatus is 100 to 140° C. and the exit temperature of the drying gas from the spraying apparatus is maintained at 45 to 70° C. Some embodiments provide that the exit temperature of the drying gas from the spraying apparatus is maintained within 5° C. of the minimum film-forming temperature.

According to one or more embodiments, the spray processing includes spray drying or agglomerating spray drying.

The polymer powder or a dispersion comprising the powder may further comprise an acid or acidic salt. In one or more embodiments, an acid or an acidic salt is added to the aqueous polymer dispersion before the spray processing and/or is added to the powder after the spray processing. One or more embodiments provide that, after the spray processing, the resulting polymer powder is redispersed in water and admixed with an acid or an acidic salt. In some embodiments, the acid added is an acid or an acidic salt thereof which is decomposed or evaporated under the conditions of the spray processing. According to one or more embodiments, as a result of adding the acid or the acidic salt, the pH of the aqueous dispersion, of the powder, or of the redispersion is in the range from 5 to 9. In some embodiments, adding the acid or the acidic salt results in the pH of the aqueous dispersion, of the powder, or of the redispersion being in the range from 6 to 8.

In some embodiments, a further auxiliary is added to the aqueous polymer dispersion before the spray processing.

Another aspect of the present invention provides a method of coating a pharmaceutical dosage form comprising applying a polymer powder obtained according to the first aspect as a coating composition to the pharmaceutical dosage form.

According to one or more embodiments of this aspect, the coating composition is applied to the dosage form in the form of an aqueous dispersion obtained by redispersing the polymer powder. In one or more embodiments, redispersing the polymer powder comprises stifling the powder in water with a dispersing apparatus at revolutions of greater than 5000 rpm. In other embodiments, redispersing the polymer powder comprises stifling the powder in water with a dispersing apparatus at revolutions of less than 1000 rpm.

Yet another aspect of the present invention provides a polymer powder obtained according to the first aspect. According to one or more embodiments of this aspect, the average particle size of the polymer powder redispersed in water is at most 5 times that of the parent primary dispersion. In some embodiments, the average particle size of the polymer powder redispersed in water is at most 3 times that of the parent primary dispersion. In some embodiments, the average particle size of the polymer powder redispersed in water is at most 2 times that of the parent primary dispersion.

DETAILED DESCRIPTION

Accordingly, a process for producing pulverulent, antioxidant-comprising coating compositions of aqueous polymer dispersions comprising, as component A, a polymer obtained by radical polymerization of a) N,N-diethylaminoethyl methacrylate, and b) at least one radically polymerizable compound selected from esters of α,β-ethylenically unsaturated mono- and dicarboxylic acids with $C_1$-$C_8$-alkanols, have been found, wherein the antioxidants are incorporated into the aqueous polymer dispersion in the form of a solution or a finely divided dispersion, and the aqueous dispersion is converted to powder form by spraying processes.

According to one or more embodiments, the antioxidants are introduced in the form of a "finely divided dispersion." As use herein, "finely divided" means that the average particle size is less than 20 μm.

Furthermore, a process has been found for converting the aqueous polymer dispersion stabilized with antioxidants into free-flowing powders by spraying processes, wherein the aqueous polymer dispersion is converted to free-flowing powders by spraying processes in the presence of a drying gas, where the entry temperature of the drying gas into the spraying apparatus is at least 20° C. above the glass transition temperature and at least 20° C. above the minimum film-forming temperature of the polymer and the exit temperature of the drying gas from the spraying apparatus is kept at 40 to 85° C.

According to a further embodiment, the entry temperature of the drying gas is at least 20° C. above the glass transition temperature and at least 20° C. above the dynamic glass transition temperature and at least 20° C. above the minimum film-forming temperature of the polymer and where the exit temperature of the drying gas from the spraying apparatus is 40 to 85° C.

Preferably, the entry temperature of the drying gas into the spraying apparatus is at least 40° C. above the glass transition temperature and at least 40° C. above the minimum film-forming temperature of the polymer.

According to a further embodiment, the entry temperature of the drying gas is at least 40° C. above the glass transition temperature and at least 40° C. above the dynamic glass transition temperature and at least 40° C. above the minimum film-forming temperature of the polymer.

For any of the aforementioned embodiments, the exit temperature of the drying gas may be in the range from 45 to 70° C.

According to a further preferred embodiment, the conversion to free-flowing powders takes place by agglomerating spray drying.

According to a further preferred embodiment, the polymers are partially neutralized with acids before or after the spraying process.

A further embodiment relates to carrying out a spraying process in the presence of further polymers and/or further auxiliaries.

Furthermore, the use of the powders obtained in this way as pharmaceutical coating compositions has been found. Preferably, the coating compositions are obtained by redispersion in water, the powder obtained by a spraying process being redispersed using low-shear stifling apparatuses at revolutions up to 1000 rpm. Surprisingly, it is also possible to use high-shear dispersing apparatuses at revolutions of >5000 rpm. This can take place according to the invention without the fine particles formed during the redispersion agglomerating and the preparation coagulating.

Free-flowing powders within the context of the present invention means that the powders, upon determining the flowability in accordance with DIN ISO 4324 using Pfrengle equipment without stifling aid, flow out of the funnel freely and completely.

Furthermore, the invention also relates to polymer powders obtained according to any of these processes, consisting of a polymer dispersion comprising, as component A, a polymer obtained by radical polymerization of
  a) N,N-diethylaminoethyl methacrylate, and
  b) at least one radically polymerizable compound selected from esters of α,β-ethylenically unsaturated mono- and dicarboxylic acids with $C_1$-$C_8$-alkanols, and antioxidants, where the average particle size of the polymer powder redispersed in water is at most 5 times, preferably at most 3 times, particularly preferably at most 2 times, that of the parent primary dispersion.

Average particle sizes refer here to the intensity average ascertained by light scattering.

The coating compositions used for the spraying processes are based on aqueous polymer dispersions which are obtained by radical emulsion polymerization of a monomer mixture M) comprising
  a) N,N-diethylaminoethyl methacrylate, and
  b) at least one radically polymerizable compound selected from esters of α,β-ethylenically unsaturated mono- and dicarboxylic acids with $C_1$-$C_8$-alkanols,
in an aqueous medium at a pH of at least 8.

The coating compositions in the form of aqueous polymer dispersions preferably obtain no additional organic solvents.

According to one or more embodiments of the invention, the coating compositions serve for producing pharmaceutical dosage forms which are intended to be released rapidly in the acidic environment of the stomach, i.e. the coatings are soluble in gastric juice. In some embodiments, released rapidly means that after 60 min at least 80% of the active ingredient has been released. According to some embodiments, coatings are not intended to dissolve in the oral cavity and throat in the neutral or virtually neutral environment of the saliva.

The coating compositions can be used for taste masking or for protection against moisture. The water-vapor permeability of the coatings is very low, as a result of which moisture-sensitive active ingredients are protected.

For producing the polymers by radical emulsion polymerization, reference is expressly made here to the disclosure of WO 2009/016258, in which the production and preferred embodiments with regard to production and also composition are described in detail.

In one or more embodiments, a polymer dispersion is used which is obtained from a monomer mixture M) which consists of
  43 to 47% by weight, based on the total weight of the monomers used for the polymerization, of N,N-diethylaminoethyl methacrylate a), and
  53 to 57% by weight, based on the total weight of the monomer used for the polymerization, of at least one compound b), in particular methyl methacrylate.

The polymers present in the dispersions preferably have an average molecular weight $M_w$, determined by means of gel permeation chromatography, in the range from 30 000 to 500 000, particularly preferably 60 000 to 140 000, in particular 80 000 to 120 000 g/mol. The polymers present in the dispersions Pd) preferably have a K value (determined in accordance with Fikentscher on a 1% strength solution in N-methylpyrrolidone (NMP)) in the range from 40 to 60.

The glass transition temperature $T_G$ determined by means of DSC "Differential Scanning calorimetry" is preferably in a range from 40 to 70° C., particularly preferably 52 to 62° C. Here, the samples are firstly heated to 150° C. and then rapidly cooled from 150° C. The measurement of the glass transition temperature takes place at a heating rate of 20° K/min.

The minimum film-forming temperature determined according to the method described in DIN ISO 2115 and is in the range from 40 to 70° C., preferably 50 to 65° C. The measurement accuracy of the method is in the region of plus/minus 5° C.

In one or more embodiments, the polymers present in the dispersions are essentially random copolymers.

The average particle diameter of the polymer particles present in the polymer dispersion (determined by means of analytical ultracentrifuge) is preferably in a range from 70 to 200 nm, particularly preferably from 80 to 150 nm, in particular from 90 to 120 nm. The particle size distribution is preferably essentially unimodal.

The LT value of the dispersions, determined on a 0.01% strength dispersion in water (2.5 cm cuvette, white light), is preferably at least 70%, particularly preferably at least 80%. The determination of the light transmission is described e.g. in Dieter Distler, Wässrige Polymerdispersionen [Aqueous polymer dispersions], Wiley-VCH (1999), p. 40.

The solids content of the dispersions used for the spraying processes is preferably 10 to 50% by weight, particularly preferably 20 to 40% by weight. In the case of a prior purification of the dispersion by means of ultrafiltration, the dispersions used may have solids contents which are within these ranges before and after the ultrafiltration. It is of course likewise possible to subject a dilute polymer dispersion to concentration by ultrafiltration before the spraying process.

The redispersible polymer powders used for taste masking have, in water at a solids content of 20% by weight, low viscosities of preferably less than 300 mPas, particularly preferably less than 200 mPas and in particular less than 100 mPas (values determined by means of Brookfield viscometer at 20° C. and 100 s$^{-1}$). Such viscosities are of particular importance for many applications.

According to one or more embodiments of the invention, the conversion of the aqueous polymer dispersions to the powder form takes place by means of spray processes. Suitable spray processes are in principle spray drying, agglomerating spray drying, spray granulation (spray fluidized-bed drying) or spray agglomeration.

The conditions specified below for carrying out the atomization and drying refer to all embodiments of the spraying process which can be carried out in principle, whether normal spray drying, spray granulation or agglomerating spray drying.

The atomization preferably takes place as hydrodynamic atomization as a result of liquid pressure or air pressure via nozzles such as, for example, single-material or multiple-material nozzles or via atomizing disks.

Suitable spraying apparatus are conventional spray towers into which the polymer dispersion to be atomized is introduced from above. The polymer powders obtained can be discharged at the lower end and be separated off from the drying-gas steam in a downstream cyclone.

Drying gases which can be used are air or inert gases such as nitrogen, argon or helium. The drying gases can be introduced countercurrently or cocurrently to the liquid droplets produced by the atomization through the spraying apparatus. The drying gas is preferably used cocurrently. The entry temperature of the drying gas is kept at least 20° C., preferably at least 40° C., above the glass transition temperature and, according to one embodiment, also at least 20° C., preferably at least 40° C., above the dynamic glass transition temperature and at least 20° C., preferably at least 40° C., above the minimum film-forming temperature of the polymer. The entry temperature of the drying gas into the spraying apparatus is particularly preferably kept at 100 to 140° C. and the exit temperature of the drying gas from the spraying apparatus is kept at 45 to 70° C. In some embodiments, the entry temperature of the drying gas into the spraying apparatus is kept at 110 to 130° C. and the exit temperature of the drying gas from the spraying apparatus is kept at 50 to 60° C.

The exit temperature of the drying gas may be in the same temperature range plus/minus 5° C. as the minimum film-forming temperature.

The evaporation of the water in the spraying apparatus can take place either atmospheric pressure or at 0.06 to 0.12 MPa.

While carrying out the spraying processes, polymeric spraying auxiliaries such as polyvinyl alcohols, mixtures of polyvinyl alcohol and one of polyethylene glycol as graft base and polyvinyl alcohol side chains (commercially available as Kollicoat® Protect), polyvinylpyrrolidones, alkylated and/or hydroxyalkylated celluloses, starch derivatives, ligninsulfonates, polyacrylic acids or polyacrylamides can also be added to the aqueous polymer dispersions. Suitable amounts of such spraying auxiliaries are in the range from 0.1 to 30, preferably 1 to 10% by weight, based on the solids content.

Furthermore, antiblocking agents can also be added to the aqueous polymer dispersions. Suitable antiblocking agents are e.g. aluminum silicates such as bentonite, also kieselguhr, colloidal silica, precipitated silica, diatomaceous earth, calcium carbonate, titanium dioxide, zinc oxide, magnesium silicates such as talc or tricalcium phosphate. Suitable amounts of such antiblocking agents are in the range from 0.1 to 15, preferably 0.5 to 5% by weight, based on the solids content.

In principle, customary coating auxiliaries can also be added to the aqueous polymer dispersions. Suitable auxiliaries may be: aroma substances, taste-improving substances, sweetening agents (sugars, sugar alcohols, sweeteners such as aspartame, saccharine-Na, sodium cyclamate), glidants, wetting agents, release agents, antisticking agents, stabilizers, antioxidants, pore formers, neutralizers, luster agents, dyes, pigments, disinfectants or preservatives, thickeners or plasticizers. Suitable auxiliaries are described e.g. in Fiedler, H. P. Lexikon der Hilfsstoffe für Pharmazie, Kosmetik and angrenzende Gebiete [Lexicon of auxiliaries for pharmacy, cosmetics and related fields], 4th edition, Aulendorf: ECV-Editio-Cantor-Verlag, 1996.

As already mentioned, one embodiment of the invention relates to conventional spray drying, during which the aqueous polymer dispersion to be dried is atomized and dried in the gas stream of the drying gas and in this way converted to powder form.

According to a further embodiment, the conversion to powder can take place by a spray granulation. For this purpose, the aqueous polymer dispersion to be dried is likewise atomized and the particles generated then come into contact in a fluidized bed with seed particles that have been introduced as initial charge. As a result of this bringing of the seed particles into contact with the droplets of the aqueous polymer dispersion, the seed particles grow to give larger granule particles, with the formation of an onion-peel-like structure around the particle used as seed material.

According to one or more embodiments of the invention, conversion to the powder form takes place with the help of agglomerating spray drying. Here, the polymer dispersion is atomized in a spray tower as described above, while fine dust which is removed from the drying zone, is at the same time blown into the atomizing zone, in which the aqueous polymer dispersion is present in the form of fine droplets. The fine dust particles stick together here to give relatively large aggregates with a blackberry-shaped structure. Additionally, a fluidized bed can also be connected, in which the water content of the particles formed can be further reduced. The resulting aggregates can have particle sizes from 150 to 1000 μm, preferably from 200 to 500 μm. In this embodiment too, the entry temperature is selected at least 20° C. and preferably at least 40° C., above the glass transition temperature, and, according to one embodiment, also at least 20° C., preferably at least 40° C., above the dynamic glass transition temperature and at least 20° C., preferably at least 40° C., above the minimum film-forming temperature of the polymer, and the exit temperature of the drying gas from the spray apparatus is selected at 40 to 85° C., preferably at 45 to 70° C. Preferably, the entry temperature of the drying gas into the spraying apparatus is kept at 100 to 140° C. and the exit temperature of the drying gas from the spraying apparatus is kept at 45 to 70° C. In some embodiments, the entry temperature of the drying gas into the spraying apparatus is kept at 110 to 130° C. and the exit temperature of the drying gas from the spray apparatus is kept at 50 to 60° C. The blackberry-shaped structures obtained by spray agglomeration are virtually dust-free and exhibit particularly advantageous behavior upon redispersion.

In all of the embodiments specified above, spraying auxiliaries such as e.g. aluminum silicates such as bentonite, kieselguhr, colloidal silica, precipitated silica, diatomaceous earth, calcium carbonate, titanium dioxide, zinc oxide, magnesium silicates such as talc or tricalcium phosphate can be blown in to the spray tower during the spraying process in amounts of from 0.1 to 15, preferably 0.5 to 5% by weight, based on the polymer powder.

The residual solvent content is usually not more than 5% by weight, based on the solids content of the powder. In total, the particle sizes of the powder formed by spray processes are governed by the particular variant. In the case of a normal spray drying, particle sizes from 10 to 150 µm can be achieved. In the case of a spray granulation, such as, for example, a spray fluidized-bed drying, larger particle sizes from 150 up to 1000 µm can be achieved. In the case of agglomerating spray drying, particle sizes from 150 to 1000 µm can be achieved.

According to a further embodiment, acids are added to the polymer. Preferably, amounts of acid are added such that the basic groups are present partially in the form of the acid salts. Preferably, 1 to 20 mol %, particularly preferably 2 to 15 mol %, of the basic groups are neutralized. This can take place before or after the spray drying. Thus, for example, the acid can be added to the aqueous polymer dispersion before the spray drying. According to another embodiment, the acid can also be added before or during the redispersion. If the incorporation of the acid takes place before the spray drying, then it can be stirred into the aqueous dispersion by means of customary processes. In the case of addition after the spray drying, the incorporation of the acid into the polymer powder takes place such that firstly the polymer powder is coarsely predispersed in water by means of a simple stirrer, then the acid is added and complete redispersion is achieved by further stifling. The redispersion is very rapid and therefore even after 10 min, finely divided dispersates are present. In a modified procedure, it is also possible to firstly introduce the acid as initial charge in water and to add the polymer powder to this with stifling. It is also possible to firstly mix polymer powder and acid and to introduce this powder mixture into water.

Suitable acids are inorganic acids or acid salts such as carbonic acid (injection of carbon dioxide), ammonium hydrogencarbonate, sodium hydrogencarbonate, hydrochloric acid, sulfuric acid or phosphoric acid or phosphoric acid salts such as sodium dihydrogenphosphate. Also of suitability are organic acids such as tartaric acid, citric acid, lactic acid, glycolic acid, malic acid, malonic acid, maleic acid, succinic acid, fumaric acid, aspartic acid, glutamic acid, gluconic acid or further physiologically compatible acids. Polymeric acids on a natural and/or synthetic base are of course also possible. The specified acids are suitable for all of the described embodiments.

According to a further embodiment of the invention, acids which are decomposed or which evaporate under the conditions of the spraying process are used. According to this embodiment, the polymers are present before and during the spraying process in neutralized or partially neutralized form, whereas in the resulting powder the free basic form is present again.

The amounts by weight of acids to be used in individual cases is governed by the particular molecular weight and the above-described desired degree of neutralization.

Preferably, the treatment with acids is carried out such that the pH of the aqueous dispersion, of the powder or of the water-redispersed powder is in the range from 5 to 9.

In some embodiments, the addition of the acid or of the acidic salt is added such that the pH of the aqueous dispersion, of the powder or of the water-redispersed powder is in the range from 6 to 8.

Coating compositions can be produced e.g. by intimately mixing by redispersing the polymer powder obtained according to the invention to give an aqueous polymer dispersion, to which preferably at least one further auxiliary is added.

For stabilization, the polymer dispersions are treated, before being converted to the powder form, as mentioned, with sparingly water-soluble antioxidants. The term "antioxidants" is known by the person skilled in the art (see e.g. Römpp—Lexikon der Chemie [Lexicon of chemistry], 9th edition, 1989, Georg-Thieme-Verlag, Stuttgart) and refers to substances which are supposed to inhibit or prevent undesired changes caused by oxygen or other oxidative processes. According to one or more embodiments of the invention, suitable antioxidants for stabilizing the coating compositions are antioxidants that are sparingly soluble in water, i.e. antioxidants whose solubility in water is not more than 1 g/l at 20° C.

According to one or more embodiments of the invention, suitable antioxidants are primarily the lipophilic substances tocopherol, tocopherol acetate, ascorbyl palmitate, ascorbyl stearate, t-butylhydroquinone, t-butylhydroxyanisole, t-butylhydroxytoluene, octyl gallate or dodecyl gallate or combinations thereof.

Incorporation of the antioxidants in the form of a solution in an organic solvent.

According to one embodiment of the invention, the antioxidants used are dissolved in an organic solvent. Suitable organic solvents are those solvents which on the one hand are sufficiently miscible with water that a concentration of at least 10% by weight in water can be achieved, but on the other hand are also able to dissolve the sparingly water-soluble antioxidants. Suitable solvents are alcohols such as e.g. ethanol or isopropanol, ketones such as e.g. acetone, methyl ethyl ketone and esters such as e.g. methyl acetate. Usually, these solvents have boiling points below 100° C. The antioxidants can be brought into organic solution in a per se customary manner. The concentration is selected such that 10 to 1000 g of antioxidant are used per liter of solvent. Overall, the amount of organic solvent is selected such that 1 to 20% by weight of solvents, based on the weight of the aqueous dispersion, are used.

According to a further embodiment, the antioxidants can be incorporated into the aqueous dispersion in the form of an aqueous micellar solution. For this, the substances are brought into solution in the presence of solubilizing substances ("solubilizers") (re the term "solubilization", see Rompp-Chemielexikon [Römpp chemistry Lexicon], 9th edition). Suitable solubilizers are surfactants such as e.g. sodium docusate or sodium dodecylsulfate, ethoxylated fats, ethoxylated fatty acids, ethoxylated fatty alcohols or polymeric solubilizers.

Suitable polymeric solubilizers are in particular amphiphilic copolymers. Amphiphilic copolymers are understood as meaning copolymers which are composed of hydrophilic and hydrophobic segments. The segments can also have a LCST (Lower Critical Solution Temperature). The segments are for their part polymer chains which, on account of their composition and/or the monomers used for producing the segments, are either hydrophilic or hydrophobic. The amphiphilic copolymers can be block polymers or graft polymers. Besides linear block polymers, the structure of the copolymer can also be comb-like or star-like. In the case of the graft polymers, either hydrophobic side chains and a hydrophilic graft base may be present, or hydrophilic side chains and a hydrophobic graft base. The side chains may either be grafted to or grafted on. Suitable amphiphilic copolymers are disclosed for example in WO 2007/017452, WO 2007/051743, WO 2007/065845 and WO 2007/065846, to the description of which with regard to suitable amphiphilic copolymers and their production reference is hereby made. Further amphiphilic copolymers are for example poloxamers.

Suitable hydrophilic segments are N-vinyllactam homopolymer or copolymer chains, in particular N-vinylpyrrolidone-containing polymers, as well as polyvinyl alcohol chains or polyethers.

Suitable hydrophobic segments are, for example, homopolymers or copolymers of N-vinyl acetate. A suitable comonomer is for example N-vinylcaprolactam.

A preferred polymeric solubilizer is a graft copolymer commercially available under the name Soluplus®, BASF SE with PEG 6000 as graft base and a copolymer side chain produced from vinyl acetate and N-vinylcaprolactam.

Also of suitability for producing the micellar solution are all surfactants which have an HLB of more than 12. Such surfactants are described in "Fiedler, Encyclopedia of Excipients", Editio Cantor Verlag. Sixth edition, 2007, page 112-119.

The aqueous antioxidant solubilizates may comprise 0.5 to 30% by weight, preferably 1 to 20% by weight, of antioxidant and 1 to 50% by weight, preferably 1 to 30% by weight, of solubilizer. In some embodiments, the amount is selected such that 1 to 40% by weight of aqueous antioxidant solubilizate, based on the weight of the aqueous dispersion, are used.

According to a further embodiment of the invention, the sparingly water-soluble antioxidants are incorporated into the aqueous dispersion of the polymeric coating composition in the form of finely divided aqueous dispersions. In this connection, dispersions is the term used to refer to two-phase systems which may be either solid/liquid (suspensions) or liquid/liquid (emulsions). The average particle size (d4,3) of the antioxidants here may be less than 20 µm, preferably less than 10 µm, particularly preferably less than 3 µm.

Thus, the antioxidants can be dissolved in emulsifiers and then dispersed in water. However, the antioxidants can also be added directly to water and be dispersed with the aid of emulsifiers using high-shear dispersing tools. Particular preference is given here to heating the preparation to a temperature above the melting point of the antioxidant, as a result of which an emulsion is formed. This hot emulsion can be added directly to the polymer dispersion with stirring. Alternatively, it can also be cooled beforehand, as a result of which a finely divided suspension is formed. It is particularly preferred to add the hot emulsion to a polymer dispersion, which likewise has a temperature above the melting point of the antioxidant.

Suitable emulsifiers are in principle all classes of interface-active substances with an HLB value of >10 (re the Hydrophilic-Lipophilic Balance value, see Fiedler, Encyclopedia of Excipients, Editio Cantor Verlag Sixth edition, 2007, page 112-119). Suitable emulsifiers are in principle all ethoxylated fatty acids, ethoxylated fatty alcohols, ethoxylated fatty acid ethers or ethoxylated fatty acid esters with corresponding HLB values. Corresponding ethoxylated sorbitan, stearyl, oleyl, lauryl or palmityl derivatives, for example Solutol® HS (Macrogol 15 hydroxystearate) or ethoxylated hydrogenated castor oil, such as, for example, Cremophor® RH40 (ethoxylated with 40 ethylene oxide units) or the corresponding Eumulgin® grades, for example, are suitable. Further suitable emulsifiers are poloxamers (polyethylene oxide-polypropylene oxide block copolymers).

The aqueous antioxidant/emulsifier dispersions may comprise 1 to 50% by weight, preferably 2 to 30% by weight, of antioxidant and 0.1 to 30% by weight, preferably 0.5 to 10% by weight, of emulsifier. In some embodiments, the amount is selected such that 1 to 40% by weight of aqueous antioxidant/emulsifier dispersion, based on the weight of the aqueous polymer dispersion, are used.

According to one or more embodiments of the invention, the antioxidants are used in the form of a so-called "solid solution". The term "solid solution" is known to the person skilled in the art and refers to a molecularly dispersed distribution of one solid in another solid. In the present case, the antioxidants can be incorporated as solid solutions into a suitable solid solubilizer or into a polymeric protective colloid. The resulting solid solution can then be incorporated directly into the aqueous coating composition dispersion in solid form or be converted beforehand into a micellar aqueous solution or into a colloidal solution and then be incorporated into the aqueous coating composition dispersion. The solid solutions can for example be produced by dissolving the antioxidants together with the solubilizer or the protective colloid in a suitable solvent and then evaporating the solvent.

According to some embodiments, the solid solution is produced by melt extrusion, where antioxidants and solubilizers or polymeric protective colloids are melted together and then extruded, molded and solidified. The granular solid melt extrudates obtained after extrusion can be incorporated particularly advantageously into the aqueous dispersion of the polymeric coating composition. Suitable matrix polymers and protective colloids for solid solutions here are the amphiphilic copolymers already mentioned, in particular Soluplus®, or poloxamers such as Lutrol® F86, but also nonamphiphilic polymers such as e.g. polyvinylpyrrolidones, vinylpyrrolidone-vinyl acetate copolymers, polyethylene glycols, polyvinyl alcohols, polyvinyl alcohol-polyethylene glycol graft copolymers or hydroxyalkylated celluloses.

Coating compositions can be produced e.g. by intimately mixing by redispersing the polymer powder obtained according to the invention to give an aqueous polymer dispersion, to which preferably at least one further auxiliary is added.

According to one or more embodiments, silicon dioxide is added to the resulting polymer powder during or after the spraying process.

Suitable additional auxiliaries may be: aroma substances, taste-improving substances, sweetening agents (sugars, sugar alcohols, sweeteners such as e.g. aspartame, saccharine-Na, sodium cyclamate), glidants, wetting agents, release agents, antisticking agents, stabilizers, antioxidants, pore formers, neutralizing agents, luster agents, dyes, pigments, disinfectants or preservatives, thickeners, plasticizers etc. Such substances are described e.g. in Fiedler, H. P. Lexikon der Hilfsstoffe für Pharmazie, Kosmetik and angrenzende Gebiete [Lexicon of auxiliaries for pharmacy, cosmetics and related fields], 4th edition, Aulendorf: ECV-Editio-Cantor-Verlag, 1996.

According to one embodiment of the invention, the N,N-diethylaminoethyl methacrylate-based polymer powder is ground before the redispersion in water for producing the coating composition. The grinding can also take place in the presence of the stated additional auxiliaries.

Customary amounts of the auxiliaries are in a range from in each case 0 to 70% by weight, preferably 0 to 60% by weight, in particular 1 to 50% by weight, based on the total weight of the solid of the coating composition.

The coating composition obtained from the powders according to the invention can, however, also be applied to the pharmaceutical dosage forms in powder form. The application can also take place in aqueous form by granulation, pouring, spreading or by means of spray application.

In some embodiments, the application uses aqueous polymer dispersion obtained by redispersing. In principle, any dispersing apparatus is suitable for the redispersion. In this connection, the redispersion preferably takes place with the application of low shear forces, preferably by means of a blade, propeller, anchor stirrer or a comparable stirring tool. The polymer powders according to the invention are hereby redispersed spontaneously and rapidly. The redispersion of the polymer powders in water is usually completed in 10 min.

Further components required for the coating application can be added to these redispersed preparations. Such components are in particular plasticizers such as e.g. triethyl citrate, tributyl citrate, diethyl sebacate, dibutyl sebacate, acetyl triethyl citrate.

Surprisingly, the finely divided dispersions also withstand very high shear forces such as for example in a rotor-stator apparatus, which is also called Ultra-turrax or a colloid mill. The introduction of high shear forces is regulated in a rotor-stator apparatus via the number of revolutions of the apparatus. Preferably, the redispersion takes place with the help of a dispersing apparatus at <5000 rpm. This process is particularly advantageous if further coarsely particulate additives or agglomerated additives additionally have to be incorporated into the dispersion which necessitate a special comminution. The separate comminution of these additives in water and subsequent addition to the redispersed polymer powder is thus dispensed with.

In one particular embodiment, the polymer powders redispersable according to the invention are mixed with further customary coating constituents and/or additives described above to produce so-called ready-to use preparations which comprise all of the required constituents of a coating. These are present in powder or granule form. The user only needs to stir them into water to produce a ready-to-spray suspension. These ready-to-use preparations are produced by dry mixing, grinding, compaction or granulation of the constituents using a granulating liquid, followed by a drying step. In particular, acids or acidic salts which assist the redispersion can be incorporated in this way.

Unless stated otherwise, all of the data within the context of the present invention relating to the average particle size of powders in the micrometer range is the volume average of the particle diameters (d4,3 value) determined by means of light diffraction.

The coating compositions according to the invention can additionally comprise at least one further polymer component. In this connection, mixtures of at least two dispersions, at least one dispersion and at least one solution, at least one dispersion and at least one powder, at least two powders, etc. can be used.

The coating compositions from according to the invention are suitable for dosage forms of in principle any desired pharmaceutical active ingredients, which can preferably be administered in isolated or protected form, such as antidepressants, beta receptor blockers, antidiabetic agents, analgesics, antiphlogistics, antirheumatics, antihypotensives, antihypertensives, psychoactive drugs, tranquilizers, antiemetics, muscle relaxants, glucocorticoids, agents for treating ulcerative colitis or Crohn's disease, antiallergic agents, antibiotics, antiepileptics, anticoagulants, antimycotics, antitussives, arteriosclerotic agents, diuretics, enzymes, enzyme inhibitors, gout remedies, hormones and inhibitors thereof, cardiac glycosides, immunotherapeutic agents and cytokines, laxatives, antilipanic agents, gastrointestinal therapeutic agents, antimigrane agents, preparation of mineral substances, otologic agents, agents to treat Parkinson's disease, thyroid therapeutic agents, spasmolytics, platelet aggregation inhibitors, vitamins, cytostatics and metastasis inhibitors, phytopharmaceuticals, chemotherapy agents, nutraceuticals, vitamins, carotenoids and amino acids.

Examples of suitable active ingredients are: acarbose, non-steroidal antirheumatics, cardiac glycosides, acetylsalicylic acid, virustatic agents, aclarubicin, aciclovir, cisplatin, actinomycin, α- and β-sympathomimetics, allopurinol, alosetron, alprostadil, prostaglandins, amantadine, ambroxol, amlodipine, methotrexate, 5-aminosalicylic acid, amitriptyline, amlodipine, amoxicillin, anastrozole, atenolol, atorvastatin, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cephalosporins, celetoxib, cetirizine, chenodeoxycholic acid, ursodeoxycholic acid, theophylline and theophylline derivatives, trypsin, cimetidine, clarithromycin, clavulanic acid, clindamycin, clobutinol, clonidine, cotrimoxazole, codeine, caffeine, vitamin D and derivatives of vitamin D, colestyramine, cromoglycic acid, coumarin and coumarin derivatives, cysteine, cytarabine, cyclophosphamide, cyclosporin, cyproterone, cytarabine, dapiprazole, desogestrel, desonide, dihydralazine, diltiazem, ergot alkaloids, dimenhydrinate, dimethylsulfoxide, dimeticone, dipyridamole, domperidone and domperidone derivatives, donepzil, dopamine, doxazosin, doxorubicin, doxylamine, dapiprazole, benzodiazepine, diclofenac, glycoside antibiotics, desipramine, econazole, ACE inhibitors, enalapril, ephedrine, epinephrin, epoetin and epoetin derivatives, morphinanes, calcium antagonists, irinotecan, modafinil, orlistat, peptide antibiotics, phenytoin, riluzole, risedronate, sildenafil, topiramate, macrolide antibiotics, esomeprazole, estrogen and estrogen derivatives, gestagen and gestagen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, flunarizine, fluorouracil, fluoxetine, flurbiprofen, ibuprofen, flutamide, fluvastatin, follitropin, formoterol, fosfomycin, furosemide, fusidic acid, galantamine, gallopamil, ganciclovir, gemfibrozil, gentamicin, ginkgo, St. John's wort, glibenclamide, urea derivatives as oral antidiabetics, glucagon, glucosamine and glucosamine derivatives, glutathione, glycerol and glycerol derivatives, hypothalamus hormones, goserelin, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramin, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives; evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, orlistat, oseltamivir, oxaceprol, oxacillin, oxiconazole, oxymetazoline, pantoprazole, paracetamol, paroxetine, penciclovir, oral penicillin, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, rosiglitazone, roxatidine, roxithromycin, ruscogenin, rutoside and rutoside derivatives, sabadilla, salbutamol, salmeterol, scopolamine, selegiline, sertaconazole, sertindole, sertraline, silicates, simvastatin, sitosterol, sotalol, spaglumic acid, sparfloxacin, spectinomycin, spiramycin, sirapril, spironolactone, stavudine, streptomycin, sucralfate, sufentanil, sulbactam, sulfonamides, sulfasalazine, sulpiride, sultamicillin, sultiame, sumatriptan, suxamethonium chloride, tacrine, tacrolimus, taliolol, tamoxifen, taurolidine, tazarotene, tegaserod, temazepam, teniposide, tenoxicam, terazosin, terbinafine, terbutaline, terfenadine, terlipres sin, tertatolol, tetracyclines, tetryzoline, theobromine, theophylline, butizine, thiamazole, phenothiazines, thiotepa, tiagabine, tiapride, propionic acid derivatives, ticlopidine, timolol, tinidazole, tioconazole, thioguanine, thioxolone, tiropramide, tizanidine, tolazoline, tolbutamide, tolcapone, tolnaftate, tolperisone, topotecan, torasemide, antiestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpine, troxerutin, tulobuterol, tyramine, tyrothricin, urapidil, ursodeoxycholic acid, chenodeoxycholic acid, valaciclovir, valdecoxib, valproic acid, vancomycin, vecuronium chloride, venlafaxine, verapamil, vidarabine, vigabatrin, viloxazine, vinblastine, vincamine, vincristine, vindesine, vinorelbine, vinpocetine, viquidil, warfarin, xantinol nicotinate, xipamide, zafirlukast, zalcitabine, zanamivir, zidovudine, zolmitriptan, zolpidem, zopiclone, zotepine and the like.

If desired, the active ingredients can also be used in the form of their pharmaceutically acceptable salts or derivatives, and in the case of chiral active ingredients, both optically active isomers and also racemates or diastereoisomer mixtures can be used. If desired, the compositions according to the invention can also comprise two or more pharmaceutical active ingredients.

According to the invention, the coating compositions can be used for coating extrudates, minitablets, capsules, soft capsules, granules, pellets, micropellets, microcapsules, nanocapsules or crystals.

For producing dosage forms, the coated granules, pellets, micropellets, microcapsules, crystals can be mixed with suitable auxiliaries and compacted to give tablets, which disintegrate in the aqueous environment of the oral cavity and release the coated fine shaped articles again. Of particular importance in this connection are the so-called oral dispersibles, i.e. tablets which disintegrate in the mouth within a short time and release the taste-masked small shaped articles.

Furthermore, the coating compositions can also be used advantageously for coating tablets.

Active ingredient classes and substances which can often bring about an unpleasant bitter taste and can be formulated advantageously according to the invention are e.g.:

analgesics and antirheumatics, such as paracetamol, diclofenac, aceclofenac, ibuprofen, ketoprofen, flurbiprofen, acetylsalicylic acid, levacetylmethadol and oxycodone;

psychoactive drugs, such as promethazines, donepezil, modafinil, nefazodone, reboxetine, sertindole and sertraline;

antibiotics, such as erythromycin, roxithromycin, clarithromycin, grepafloxacin, ciprofloxacin, levofloxacin, sparfloxacin, trovafloxacin and nevirapine;

beta blockers, such as propranolol, metoprolol, bisoprolol and nebivolol;

antidiabetics, such as metformin, miglitol and repaglinide;

$H_1$ antihistamines, such as diphenhydramine, fexofenadine and mizolastine;

$H_2$ antihistamines, such as cimetidine, famotidine, roxatidine, nizatidine, ticlopidine, cetirizine and ranitidine;

vitamins such as thiamine nitrate and quinidine sulfate, amyloprilose HCl, pseudoephedrine HCl, sildenafil, topiramate, granisetron, rebamipide, quinine HCl, etc.

Also various salts of these active ingredients can be formulated correspondingly.

The exceptional taste masking results from the insolubility of the polymers according to one or more embodiments of the invention at pH values greater than 6 and the rapid solubility at pH values below 6. That is in the saliva (pH: 7.2) correspondingly coated forms are stable for a very long time and there is no contact between the bitter drug and the oral mucosa, but in the stomach at pH values from 1 to 5 there is very rapid release of the active ingredient. The dissolution is so rapid here that there is no difference in the onset of action compared with an uncoated form. As a rule, film coatings of a polymer according to the invention dissolve within 5 min in gastric juice, whereas in phosphate buffer pH 7.2 they are stable for 2 hours. Surprisingly, the film coatings also dissolve relatively quickly in media with pH values of 4.5, meaning that the administration forms produced therefrom develop a rapid effect even in anacidic patients or patients which are treated with antacids. These exceptional application properties of the coating compositions are also retained after the conversion to powders and redispersion or melting of the powders.

Surprisingly, with the help of the process according to the invention, the incorporation of sparingly water-soluble antioxidants into the polymer dispersions takes place in a manner such that the antioxidants migrate into the polymer particles and are no longer present in particulate form in the water phase. Only as a result of this can an antioxidative effect on the polymer and a corresponding protection be achieved.

In addition, surprisingly, with the help of the process according to embodiments of the invention, it is possible to convert the aqueous polymer dispersion into free-flowing powders without resulting in relatively large agglomerations and deposits in the spraying apparatus. In view of the recommendations in the prior art with regard to drying method or temperature control of the drying gases, this had not been expected by the person skilled in the art. It was also surprising that the use of high shear forces is advantageous since the person skilled in the art would normally have expected coagulation of the dispersion at shear forces.

The process according to the invention accordingly leads to polymer powders with a good particle size distribution and good application properties such as, for example, flowability. When used for producing coating compositions, the powders can be redispersed very advantageously to give finely divided dispersions.

EXAMPLES

Abbreviations Used:
Glass transition temperature: Tg
All data in % relate to % by weight.
The preparation of the polymer takes place analogously to example 1 of WO 2009/016258.
Polymer A: Methyl methacrylate/diethylaminoethyl methacrylate, weight ratio 60:40, K value 50, Tg 62° C.
Polymer B: Methyl methacrylate/diethylaminoethyl methacrylate, weight ratio 55:45, K value 49, Tg 57° C.
Polymer C: Methyl methacrylate/diethylaminoethyl methacrylate, weight ratio. 53:47, K value 52, Tg 55° C.

The K values were measured at 0.1% strength by weight in NMP. The polymers were used as 30% strength by weight aqueous dispersions with a pH of 9+/−0.3. The average particle sizes of the primary dispersions was 128, 127 and 131 nm. The glass transition temperatures were determined by means of DSC at a heating rate of 20° K/min. The minimum film-forming temperature corresponded to the Tg within the scope of the measurement accuracy of plus/minus 5° C.

When determining the average particles sizes of the powders, the (d4,3 value) was determined by means of light diffraction using a Malvern Mastersizer 2000.

When determining the average particle sizes of the redispersed powders by means of light scattering, the value was determined using a "Malvern Zetasizer nano-s" as intensity average.

Example 1

3.0 g of butylhydroxytoluene were dissolved in 50 g of ethanol and introduced, with stifling, into 1000 ml of an aqueous dispersion of polymer B with a solids content of 30%. Then, with stifling, 72.9 ml of 1 molar hydrochloric acid were mixed in. This corresponds to a degree of neutralization of 10 mol %. After stirring for 0.5 hours, this partially neutralized dispersion was spray dried in a FSD spray tower, the atomization taking place via a 1.2 mm two-material nozzle at an atomization pressure of 2.5 bar. The entry air temperature was 115° C. and the exit air temperature 58° C. The fines fraction was separated off during the spray drying and blown again in front of the spray nozzle so that spray-dried particles with an average particle size of 170 μm resulted.

The spray-dried product was redispersed in water to give a spray suspension with a solids content of 20% by stifling using a paddle stirrer for 15 min. Measurement of the particle size by means of light scattering gave a value of 135 nm.

Example 2

6.0 g of tocopherol were dissolved in 20.0 g of Cremophor RH 40 and then the mixture was diluted with 80.0 g of water. This solubilizate was slowly added, with stifling, to 1000 ml of an aqueous dispersion of polymer A with a solids content of 30%, further stirred for 1 hour and spray dried in a spray tower. The atomization took place here via a 1.2 mm two-material nozzle at an atomization pressure of 3.0 bar. The drying gas was introduced tangentially in the entry region of the spray dryer and the dried product was separated off in a cyclone. The entry air temperature was 107° C. and the exit air temperature 55° C. The average particle size of the powders was 32 μm.

100 g of spray-dried product were introduced into 900 ml of water, into which 2.30 g of succinic acid had been dissolved beforehand. The preparation was stirred for 20 min using a propeller stirrer. Measurement of the particle size by means of light scattering gave a value of 139 nm.

Example 3

4.5 g of butylhydroxytoluene were added to 30.0 g of water, heated to 80° C., subjected to microfine emulsification using an Ultra-turrax for 10 min at 10 000 rpm and then slowly added, with stifling, to 1000 ml of a 75° C.-hot aqueous dispersion of polymer A with a solids content of 30%. This preparation was further stirred for 1 hour and spray dried in a spray tower. The atomization took place here via a 1.2 mm two-material nozzle at an atomization pressure of 3.0 bar. The drying gas was introduced tangentially in the entry region of the spray dryer and the dried product was separated off in a cyclone. The entry air temperature was 108° C. and the exit air temperature 55° C. The average particle size of the powders was 34 μm.

150 g of spray-dried product were introduced into 850 ml of water and the preparation was treated for 20 min using an Ultra-turrax at 12 000 rpm. Measurement of the particle size by means of light scattering gave a value of 230 nm.

Example 4

100 g of butylhydroxyanisole were processed in an extruder at 140° C. with 400 g of Soluplus to give a solid solution. The resulting strands were reduced to ca. 2 mm in size. 20.0 g of this solid solution were added to 1000 ml of an aqueous dispersion of polymer B with a solids content of 30% and the mixture was further stirred for 1 hour. Then, with stifling, 36.5 ml of 1 molar hydrochloric acid ware added. This corresponds to a degree of neutralization of 5 mol %. This partially neutralized dispersion was spray dried in a FSD spray tower, the atomization taking place via a 1.2 mm two-material nozzle at an atomization pressure of 3.0 bar. The entry air temperature was 125° C. and the exit air temperature 56° C. The fines fraction was separated off during the spray drying and blown again in front of the spray nozzle, so that spray-dried particles with an average particle size of 180 μm resulted. During the spraying process, colloidal silicon dioxide with a BET surface area of 200 m²/g was blown into the tower in an amount of 0.5%, based on the total mass of the polymer powder.

The spray-dried product was redispersed in water to give a spray suspension with a solids content of 20% by stifling using a paddle stirrer for 20 min. Measurement of the particle size by means of light scattering gave a value of 140 nm.

Example 5

5.0 g of butylhydroxytoluene and 10.0 g of docusate sodium were added to 50.0 g of water and heated to 50° C. with stirring. Following dissolution of the butylhydroxytoluene, this preparation was mixed with 1000 ml of an aqueous dispersion of polymer C with a solids content of 30%, with stifling. After adding 1.31 g of malonic acid, which corresponds to a degree of neutralization of 5 mol %, this partially neutralized dispersion was mixed with 200 ml of a 40% strength suspension of talc and spray dried in a FSD spray tower, the atomization taking place via a 1.2 mm two-material nozzle at an atomization pressure of 3.0 bar. The entry air temperature was 137° C. and the exit air temperature 59° C. The fines fraction was separated off during the spray drying and blown again in front of the spray nozzle, so that spray-dried particles with an average particle size of 185 μm resulted.

The spray-dried product was redispersed in water to give a spray suspension with a solids content of 20% by stifling using a paddle stirrer for 15 min. Measurement of the particle size by means of light scattering gave a value of 145 nm for the polymer particles.

Example 6

100 g of polymer powder prepared as in example 3 were mixed with 50 g of very finely ground talc, 4 g of indigotin lake and 2 g of succinic acid in a Turbula mixer.

Following the redispersion of this preparation in water to give a 15% strength suspension using a propeller stirrer, a particle size of the polymer particles of 160 nm was produced.

Example 7

The preparation produced as in example 6 was admixed with 13.0 g of triethyl citrate, stirred for one hour and applied to tablet cores by spraying.
Spraying Conditions:

| Machine | Horizontal drum coater |
|---|---|
| Entry air temperature | 54° C. |
| Spraying pressure | 0.2 MPa |
| Shaping air pressure | 0.1 MPa |
| Spray nozzle | Schlick 930/1 mm |
| Entry air rate | 200 m³/h |
| Spraying rate | 30 g/min |

The resulting film tablets had a smooth, shiny, taste-masking coating which did not change even upon stress storage below 40° C.

The invention claimed is:

1. A process for producing pulverulent, antioxidant-comprising pharmaceutical coating compositions, the process comprising:
   providing an aqueous polymer dispersion comprising one or more antioxidants and, as component A, a polymer obtained by radical polymerization of
   a) N,N-diethylaminoethyl methacrylate, and
   b) at least one radically polymerizable compound selected from esters of α,β-ethylenically unsaturated mono- and dicarboxylic acids with $C_1$-$C_8$-alkanols,
   wherein the antioxidants are incorporated into the aqueous polymer dispersion in the form of a solid solution of the antioxidants in surfactants or polymers or of a dispersion comprising emulsifiers with a hydrophilic-lipophilic balance value greater than 10; and
   spray processing the aqueous polymer dispersion to provide a pharmaceutical powder form.

2. The process according to claim 1, wherein one or more antioxidants are sparingly water-soluble.

3. The process according to claim 1, wherein the antioxidants are incorporated in the form of a solution in an organic solvent or as a micellar aqueous solution comprising a solubilizer.

4. The process according to claim 3, wherein the micellar solution of the antioxidants comprises surfactants or amphiphilic copolymers as solubilizers.

5. The process according to claim 1, wherein the solid solution of the antioxidants in surfactants or polymers is obtained by melt extrusion.

6. The process according to claim 1, wherein the antioxidants are incorporated in amounts of from 0.1 to 10.0% by weight, based on component A.

7. The process according to claim 1, wherein the aqueous polymer dispersion is converted to powder by spraying processes in the presence of a drying gas, wherein the entry temperature of the drying gas into the spraying apparatus is at least 20° C. above the glass transition temperature and is at least 20° C. above the minimum film-forming temperature of the polymer of the polymer and the exit temperature of the drying gas from the spraying apparatus is maintained at 40 to 85° C.

8. The process according to claim 7, wherein the entry temperature of the drying gas into the spraying apparatus is at least 40° C. above the glass transition temperature and is at least 40° C. above the minimum film-forming temperature of the polymer.

9. The process according to claim 7, wherein the entry temperature of the drying gas into the spraying apparatus is at least 20° C. above the dynamic glass transition temperature.

10. The process according to claim 7, wherein the entry temperature of the drying gas into the spraying apparatus is 100 to 140° C. and the exit temperature of the drying gas from the spraying apparatus is maintained at 45 to 70° C.

11. The process according to claim 7, wherein the exit temperature of the drying gas from the spraying apparatus is maintained within 5° C. of the minimum film-forming temperature.

12. The process according to claim 1, wherein the spray processing includes spray drying or agglomerating spray drying.

13. The process according to claim 7, wherein an acid or an acidic salt is added to the aqueous polymer dispersion before the spray processing or is added to the powder after spray processing.

14. The process according to claim 7, wherein, after the spray processing, the resulting polymer powder is redispersed in water and admixed with an acid or an acidic salt.

15. The process according to claim 13, wherein, as a result of adding the acid or the acidic salt, the pH of the aqueous dispersion or of the powder is in the range from 5 to 9.

16. A method of coating a pharmaceutical dosage form comprising applying a polymer powder obtained according to claim 1 as a coating composition to the pharmaceutical dosage form.

* * * * *